US00PP24133P3

(12) United States Plant Patent
Klemm et al.

(10) Patent No.: US PP24,133 P3
(45) Date of Patent: Dec. 31, 2013

(54) *PELARGONIUM* PLANT NAMED 'KLEPZ11229'

(50) Latin Name: *Pelargonium zonale*
Varietal Denomination: KLEPZ11229

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 135 days.

(21) Appl. No.: 13/385,931

(22) Filed: Mar. 15, 2012

(65) Prior Publication Data

US 2013/0247263 P1 Sep. 19, 2013

(51) Int. Cl.
*A01H 5/00* (2006.01)

(52) U.S. Cl.
USPC ..... Plt./329

(58) Field of Classification Search
USPC ..... Plt./329
See application file for complete search history.

(56) References Cited

U.S. PATENT DOCUMENTS

PP18,251 P2 * 11/2007 Klemm ..... Plt./329
PP19,486 P2 * 11/2008 Klemm ..... Plt./329

OTHER PUBLICATIONS

PLUTO UPOV 201303 Databse QZ Citation for 'KLEPZ11229' Oct. 15, 2011.*
PLUTO UPOV 201303 Database No Citation for 'KLEPZ11229' Nov. 15, 2011.*
PLUTO UPOV 201303 Database CA Citation for 'KLEPZ11229' Apr. 29, 2011.*
Anonymous. "Moonlight Lavender evol. *Geranium* Zonal" Ball Plant Information Accessed Sep. 19, 2013 available at www.ballhort.com/retaliers/plant_info.aspx?phid=028902331002843.*

* cited by examiner

*Primary Examiner* — Wendy C Haas
(74) *Attorney, Agent, or Firm* — Jondle Plant Sciences Division of Swanson & Bratschun, L.L.C.

(57) ABSTRACT

A new variety of *pelargonium* named 'KLEPZ11229', particularly characterized by large, round, and very shiny lavender blue flowers, medium growth habit and dark green leaves without zonation, is disclosed.

1 Drawing Sheet

Genus and species: *Pelargonium zonale.*
Variety denomination: 'KLEPZ11229'.

BACKGROUND OF THE NEW PLANT

The present invention comprises a new and distinct variety of *pelargonium*, botanically known as *Pelargonium zonale*, and hereinafter referred to by the variety name 'KLEPZ11229'. The new variety is the result of a controlled cross conducted in July 2004 in Stuttgart, Germany between the female *pelargonium* parent, 'PA 402' (unpatented), and the male *pelargonium* parent, 'KLEP04131' (U.S. Plant Pat. No. 18,251). A single plant selection was subsequently chosen for further evaluation and asexual propagation.

The new variety was first propagated via vegetative cuttings in September 2006 in Stuttgart, Germany and has been asexually reproduced repeatedly by vegetative cuttings in Stuttgart, Germany for approximately 6 to 8 generations. 'KLEPZ11229' has been found to retain its distinctive characteristics through successive asexual propagations via vegetative cuttings.

Plant Breeder's Rights for this variety were applied for in the following countries: Canada on Mar. 4, 2011, Switzerland on Jul. 4, 2011, the European Union on Jul. 8, 2011, and Norway on Aug. 5, 2011. 'KLEPZ11229' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Large, round, and very shiny lavender blue flowers;
2. Medium growth habit; and
3. Dark green leaves without zonation.

DESCRIPTION OF THE PHOTOGRAPH

This new *pelargonium* plant is illustrated by the accompanying photograph which shows blooms, buds, and foliage of the plant. The colors shown are as true as can be reasonably obtained by conventional photographic procedures. The photograph is of a 3-month old plant taken in early Spring 2011 grown from a rooted cutting in a 12 centimeter pot in a glass greenhouse in Stuttgart, Germany under conditions which approximate those generally used in normal horticultural practice.

DESCRIPTION OF THE NEW VARIETY

The following detailed descriptions set forth the distinctive characteristics of 'KLEPZ11229'. The data which define these characteristics were collected from asexual reproductions carried out in Stuttgart, Germany. The plant history was taken on 3-month old, un-pinched plants grown in 12 centimeter pots in a glass greenhouse in Stuttgart, Germany. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Geraniaceae.
- *Species*.—*Pelargonium zonale*.
- *Common name*.—*Pelargonium* (Geranium).
- *Denomination*.—'KLEPZ11229'.

Parentage:
- *Female parent*.—*Pelargonium* plant named 'PA 402' (unpatented).
- *Male parent*.—*Pelargonium* plant named 'KLEP04131' (U.S. Plant Pat. No. 18,251).

Plant:
- *Habit*.—Upright.
- *Height to the top of the umbels*.—15.0 cm to 25.0 cm.
- *Spread*.—Approximately 24.0 cm.
- *Life cycle*.—Spring to autumn.
- *Form*.—Round, bushy.
- *Time to produce a rooted cutting*.—18 days.
- *Time to bloom from propagation*.—Approximately 80 days.
- *Lastingness of inflorescence on the plant*.—14 days.

Stems:
- *Stem color*.—RHS 137D.
- *Pubescence*.—Present, short.
- *Stem form*.—Upright.
- *Diameter*.—0.5 cm to 0.8 cm.
- *Length*.—4.0 cm to 10.0 cm.
- *Internode length*.—0.5 cm to 1.6 cm.

Leaves:
- *Arrangement*.—Alternate.
- *Shape*.—Ivy-shaped with distinct lobes.
- *Apex*.—Round.
- *Base*.—Closed.
- *Margin*.—Crenate.
- *Surface texture* (*both surfaces*).—Dull.
- *Length*.—4.0 cm to 5.0 cm.
- *Width*.—5.0 cm to 6.0 cm.
- *Color*.—Upper surface: RHS N137B Lower surface: RHS N137D.
- *Fragrance*.—Absent.
- *Surface pubescence*.—Absent.
- *Petiole*.—Length: 12.0 cm. Diameter: 0.15 cm. Color: RHS 137D.
- *Venation pattern*.—Palmate.
- *Venation color* (*both surfaces*).—RHS 137D.

Inflorescence:
- *Flowering habit*.—Continuous.
- *Umbels*.—Length: 10.0 cm. Diameter: 10.0 cm.
- *Individual florets of the umbel*.—Depth: 2.0 cm. Diameter: 3.0 cm to 4.0 cm.
- *Flowers per umbel*.—4 to 5.
- *Umbels per plant*.—4.
- *Fragrance*.—Absent.

Flower buds:
- *Cluster shape*.—Round.
- *Cluster size*.—Length: 2.0 cm. Width: 2.0 cm. Buds per cluster: 12 to 30.
- *Bud*.—Length: 0.5 cm to 0.8 cm. Diameter: 0.3 cm to 0.5 cm. Shape: Ovate. Apex: Acute. Base: Obtuse. Margin: Entire. Color: RHS 137B.
- *Corolla*.—Diameter: 4.5 cm. Depth: 1.5 cm.

Petals:
- *Quantity per flower*.—5 to 7.
- *Shape*.—Spatulate.
- *Apex*.—Round, entire.
- *Base*.—Obtuse.
- *Margin*.—Entire.
- *Length*.—2.5 cm.
- *Width*.—2.0 cm.
- *Texture* (*both surfaces*).—Smooth.
- *Color of lobes*.—Upper lobes: Upper surface: RHS N80B. Lower surface: RHS N80C. Lower lobes (both surfaces): RHS N80D.

Sepals:
- *Quantity per flower*.—5.
- *Shape*.—Elliptic.
- *Apex*.—Acute.
- *Base*.—Open.
- *Margin*.—Entire.
- *Color*.—Upper surface: RHS 137C. Lower surface: RHS 137D.
- *Length*.—1.5 cm to 2.5 cm.
- *Width*.—0.2 cm.

Pedicel:
- *Length*.—1.5 cm.
- *Diameter*.—0.5 cm.
- *Color*.—RHS 137D.
- *Texture*.—Smooth.

Peduncle:
- *Length*.—10.0 cm to 15.0 cm.
- *Diameter*.—0.5 cm.
- *Color*.—RHS 137C.
- *Texture*.—Smooth.

Reproductive organs:
- *Stamens*.—Quantity per flower: Variable, moderate. Anther length: 0.4 cm. Filament length: 0.6 cm. Filament color: RHS 155C. Pollen amount: Moderate. Pollen color: RHS 39B to RHS 39C.
- *Pistils*.—Quantity per flower: 1. Stigma color: RHS 73D. Style length: 0.4 cm. Style color: RHS 158D. Ovary arrangement: Upright. Ovary color: RHS 140D.

Fruit and seed set: None observed.

Disease, pest, and stress resistance: No particular resistance observed.

COMPARISON WITH PARENTAL VARIETIES

'KLEPZ11229' differs from the female parent 'PA 402' (unpatented) in that 'KLEPZ11229' has dark green leaves and a medium, compact growth habit, while 'PA 402' has light green leaves and a stronger growth habit. 'KLEPZ11229' differs from the male parent 'KLEP04131' (U.S. Plant Pat. No. 18,251) in that 'KLEPZ11229' has large, round lavender blue flowers and a medium, compact growth habit, while 'KLEP04131' has smaller purple blue flowers and a smaller, compact growth habit.

We claim:

1. A new and distinct variety of *pelargonium* plant named 'KLEPZ11229' as shown and described herein.

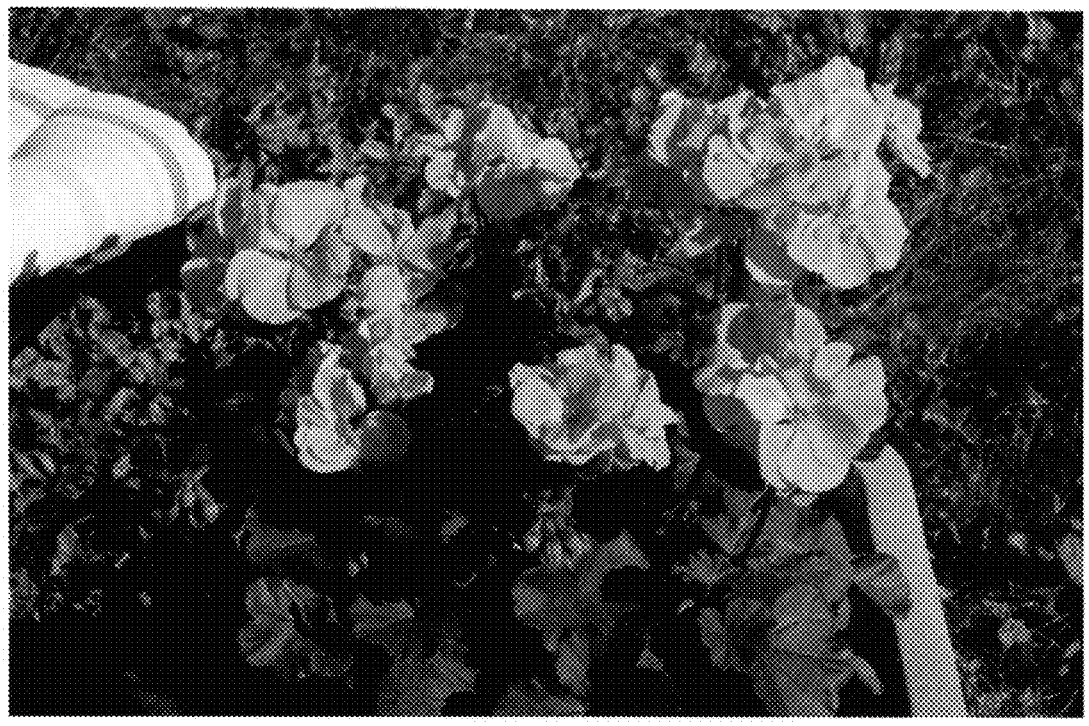

* * * * *